United States Patent
Okuro et al.

(10) Patent No.: US 6,348,615 B2
(45) Date of Patent: Feb. 19, 2002

(54) PROCESS FOR PRODUCING (2R, 3S)-3-AMINO-1, 2-OXIRANE

(75) Inventors: Kazumi Okuro; Kenji Inoue, both of Hyogo (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/852,652

(22) Filed: May 11, 2001

Related U.S. Application Data

(63) Continuation of application No. 09/530,106, filed as application No. PCT/JP99/04579 on Aug. 25, 1998, now Pat. No. 6,278,002.

(30) Foreign Application Priority Data

Aug. 25, 1998 (JP) .......................................... 10-238541

(51) Int. Cl.$^7$ ....................... C07C 307/02; C07C 69/76; C07C 67/02
(52) U.S. Cl. .............................. 560/12; 560/14; 560/21; 560/24; 560/27; 560/106; 560/107; 560/110; 560/112; 560/250; 560/252
(58) Field of Search .............................. 560/12, 14, 21, 560/24, 27, 106, 107, 110, 112, 250, 252

(56) References Cited

U.S. PATENT DOCUMENTS 5,475,013 A 12/1995 Talley et al. ................. 514/311
5,559,256 A 9/1996 Gordon et al. ............... 552/303

FOREIGN PATENT DOCUMENTS

JP 6-260857 7/1994
WO WO 99/38855 8/1999

*Primary Examiner*—Ba K. Trinh
(74) *Attorney, Agent, or Firm*—Sughrue Mion, PLLC

(57) ABSTRACT

A process for producing (2R, 3S)-3-amino-4-phenylbutane-1,2-epoxide compounds which comprises treating a (2S, 3S)-3-amino-1-halo-2-hydroxy-4-phenylbutane compound or a (2S, 3S)-3-amino-4-phenylbutane-1,2-epoxide with a carboxylic acid quaternary ammonium salt or a carboxylic acid metal salt a quaternary ammonium salt and a quaternary ammonium salt, to give a (2S, 3S)-1-acyloxy-3-amino-2-hydroxy-4-phenylbutane compound, further treating the same with a sulfonic acid halide in the presence of an organic base to give a (2S, 3S)-1-acyloxy-3-amino-2-sulfonyloxy-4-phenylbutane compound, furthermore treating said compound with an inorganic base. An intermediate for the production of an HIV protease inhibitor can be produced from L-phenylalanine.

12 Claims, No Drawings

PROCESS FOR PRODUCING (2R, 3S)-3-AMINO-1, 2-OXIRANE

This is a continuation of application Ser. No. 09/530,106 now U.S. Pat. No. 6,278,002 which is a § 371 of PCT/JP99/04579, filed Aug. 25, 1998, and having a § 371 date of Sep. 1, 2000, the disclosure of which is incorporated herein by reference.

TECHNICAL FIELD

The present invention relates to a process for producing (2R,3S)-3-amino-4-phenylbutane-1,2-epoxide (hereinafter also referred to as 3-amino-1,2-oxirane), which is useful as an intermediate for the production of an HIV protease inhibitor.

BACKGROUND ART

The processes so far known for producing said (2R,3S)-3-amino-1,2-oxirane comprise starting with L-phenylalanine, reducing the carboxyl group thereof to an alcohol function, reoxidizing the same to an aldehyde function, and thereafter 1) directly causing formation of the epoxide using a dimethylsulfonium methylide (J. Org. Chem., 1985, 50, 4615; J. Med. Chem., 1992, 35, 2525), 2) converting the aldehyde to the corresponding olefin by the Wittig reaction and epoxidizing the olefin using m-chloroperbenzoic acid (J. Org. Chem., 1987, 52, 1487; J. Med. Chem. 1992, 35, 1685), 3) reacting the aldehyde with trimethylsilylmethylmagnesium chloride, converting the resulting trimethylsilylalcohol to the corresponding olefin by treatment with trifluoroboron and, as in the method 2) mentioned above, conducting epoxidation using m-chloroperbenzoic acid (EP 0532-466 A2, U.S. Pat. No. 5,514,814) or 4) converting L-phenylalanine to the diazoketone form, degradating the same with hydrochloric acid, reducing the resulting α-ketone with $NaBH_4$ and treating the resulting chlorohydrin with a base to give the epoxide (J. Med. Chem., 1994, 37, 1758), among others.

Meanwhile, there is no precedent technology for producing (2R,3S)-3-amino-1,2-oxirane compounds represented by the general formula (8) starting with a (2S,3S)-3-amino-1-chloro-2-hydroxy-4-phenylbutane compound or a (2S, 3S)-3-amino-1,2-oxirane compound as in the process of the present invention.

Referring to the above known processes, the process 1) is disadvantageous in that it is necessary to use the sulfur compound in large amounts in the step of epoxide formation, the methods 2) and 3) are disadvantageous in that it is necessary to use the peroxide, which is explosive, in large amounts, and the method 4) is disadvantageous in that it is necessary to handle the diazo compound, which is also explosive, and, in addition, the selectivity toward the desired (2R,3S)-chlorohydrin in $NaBH_4$ reduction is low. Thus, every process comprises a step undesirable from the viewpoint of commercial scale practicing.

SUMMARY OF THE INVENTION

In view of the problems mentioned above, the present inventors made intensive investigations in an attempt to develop a process for producing a (2R, 3S)-3-amino-1,2-oxirane compounds which can be carried out efficiently and on a commercial scale and, as a result, succeeded in developing a novel process for production which starts with a (2S, 3S)-3-amino-1-chloro-2-hydroxy-4-phenylbutane compound or a (2S, 3S) -3-amino-1, 2-oxirane compound and involves three steps, namely acyloxylation, sulfonate ester formation and treatment with a base.

Thus, the present invention relates to a process for producing (2R, 3S)-3-amino-4-phenylbutane-1,2-epoxide compounds represented by the general formula (8):

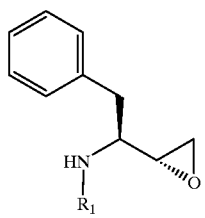

(8)

wherein $R_1$ represents an amino-protecting group, which comprises
treating a (2S, 3S)-3-amino-1-halo-2-hydroxy-4-phenylbutane compound represented by the general formula (1) or a (2S, 3S)-3-amino-4-phenylbutane-1, 2-epoxide represented by the general formula (2):

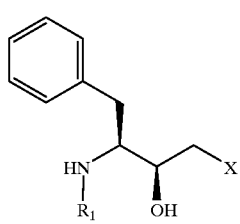

(1)

wherein $R_1$ is as defined above and X represents a halogen atom,

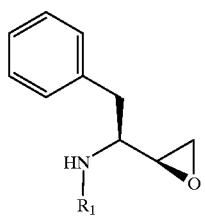

(2)

wherein $R_1$ is as defined above,
with a carboxylic acid quaternary ammonium salt represented by the general formula (3) or a carboxylic acid metal salt represented by the general formula (4):

$$R_3R_4R_5R_6N^+OCOR_2^-$$ (3)

wherein $R_2$ represents an alkyl, aryl or aralkyl group and $R_3$, $R_4$, $R_5$ and $R_6$ may be the same or different and each independently represents an alkyl or aralkyl group, $$R_2COO^-M^+$$ (4)

wherein $R_2$ is as defined above and M represents a metal atom, and a quaternary ammonium salt represented by the general formula (5):

$$R_3R_4R_5R_6N^+Y^-$$ (5)

wherein $R_3$, $R_4$, $R_5$ and $R_6$ are as defined above and Y represents a halogen atom, to give a (2S, 3S) -

1-acyloxy-3-amino-2-hydroxy-4-phenylbutane compound represented by the general formula (6):

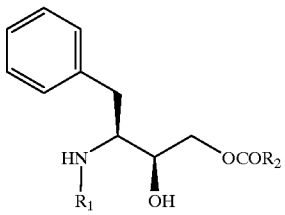

(6)

wherein $R_1$ and $R_2$ are as defined above,
further treating said (2S, 3S)-1-acyloxy-3-amino-2-hydroxy-4-phenylbutane compound with a sulfonic acid halide in the presence of an organic base
to give a (2S, 3S)-1-acyloxy-3-amino-2-sulfonyloxy-4-phenylbutane compound represented by the general formula (7):

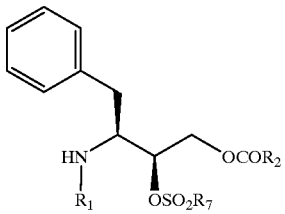

(7)

wherein $R_1$ and $R_2$ are as defined above and $R_7$ represents an alkyl, aryl or aralkyl group,
and furthermore treating said (2S, 3S)-1-acyloxy-3-amino-2-sulfonyloxy-4-phenylbutane compound with an inorganic base.

The (2S, 3S)-3-amino-1-halo-2-hydroxy-4-phenylbutane compound can be synthesized, for example, by N-protection of L-phenylalanine, which is a naturally-occurring and inexpensive substance, followed by esterification, and stereoselective reduction of the haloketone resulting from chain extension (Japanese Kokai Publication Hei-08-823756).

BEST MODES FOR CARRYING OUT THE INVENTION

The starting compound in the present process is the above-mentioned (2S, 3S)-3-amino-1-halo-2-hydroxy-4-phenylbutane compound of the general formula (1) or (2S, 3S)-3-amino-4-phenylbutane-1,2-epoxide compound of the general formula (2). In the formulas, $R_1$ represents an amino-protecting group in common use, such as a methoxycarbonyl, ethoxycarbonyl, allyloxycarbonyl, acetyl, benzoyl or chloroacetyl group, desirably a t-butoxycarbonyl or benzyloxycarbonyl group, and X represents a halogen atom such as a chlorine or bromine atom.

The acyloxylating agent to be used in the above process is the above-mentioned carboxylic acid quaternary ammonium salt of the general formula (3), or the carboxylic acid metal salt of the general formula (4) plus the quaternary ammonium salt of the general formula (5). In the formula (3), $R_2$ represents an alkyl, aryl or aralkyl group. The alkyl group is, for example, methyl, ethyl, propyl, isopropyl, butyl or isobutyl. The aryl group is, for example, phenyl or tolyl. The aralkyl group is, for example, benzyl. A methyl group is preferred as $R_2$, however. In the formula (3), M specifically includes, among others, lithium, sodium, potassium, magnesium and calcium, and is preferably sodium or potassium. $R_3$, $R_4$, $R_5$ and $R_6$ each independently represents an alkyl or aralkyl group. The alkyl group includes, among others, methyl, ethyl, propyl, butyl, pentyl, hexyl, heptyl and octyl. The aralkyl group is, for example, benzyl. Among these, butyl is preferred. Y is a halogen atom, such as a chlorine or bromine atom.

In the general formula (7) representing the sulfonate ester, $R_7$ represents an alkyl, aryl or aralkyl group. The alkyl group is, for example, methyl or ethyl. The aryl group is, for example, phenyl, p-methylphenyl or p-nitrophenyl. The aralkyl group is, for example, benzyl. Among them, methyl is preferred.

In accordance with the present invention, the above (2S, 3S)-1-acyloxy-3-amino-2-sulfonyloxy-4-phenylbutane compound (6) is first derived from the (2S, 3S)-3-amino-1-halo-2-hydroxy-4-phenylbutane compound (1) or (2S, 3S)-3-amino-1, 2-oxirane compound (2) by treatment with the carboxylic acid quaternary ammonium salt (3), for example tetrabutylammonium acetate, or with the carboxylic acid metal salt (4) and quaternary ammonium salt (5), for example calcium acetate or sodium acetate, and tetrabutylammonium chloride or tetrabutylammonium bromide.

The solvent to be used in the above step is not particularly restricted but includes, among others, acetone, acetonitrile, N,N-dimethylformamide, dimethyl sulfoxide, tetrahydrofuran, dioxane and toluene. Among them, acetone, acetonitrile and N,N-dimethylformamide are preferred.

The carboxylic acid quaternary ammonium salt (3) is used generally in an amount of 1.0 to 2.0 moles, preferably 1.2 moles, per mole of the compound (1) or (2). The carboxylic acid metal salt (4) and quaternary ammonium salt (5) are used generally in a molar ratio of (1) or (2)/carboxylic acid metal salt/quaternary ammonium salt=1.0 mole/1.0 to 5.0 moles/0.05 to 2.0 moles, preferably 1.0 mole/2.0 moles/0.05 mole.

The reaction is carried out generally at a temperature of 60° C. to 100° C., preferably 60° C. to 80° C. The reaction time is generally 5 to 24 hours, preferably about 10 to 12 hours, although it may vary depending on the reaction temperature.

After the reaction, the (2S, 3S)-1-acyloxy-3-amino-2-hydroxy-4-phenylbutane compound (6) formed can be recovered by extraction with a solvent such as ethyl acetate and can be further purified by such techniques as column chromatography and/or recrystallization.

The sulfonic acid esterification of the (2S, 3S)-1-acyloxy-3-amino-2-hydroxy-4-phenylbutane compound (6) is carried out in the presence of an organic base by using 1.0 to 3 moles of a sulfonic acid halide per mole of the compound (6). The sulfonic acid halide includes, among others, sulfonyl chlorides, specifically methanesulfonyl chloride, toluene-sulfonyl chloride and the like. As the organic base, there may be mentioned tertiary-amines, specifically pyridine, triethylamine, tripropylamine, methyldiisopropylamine, ethyldiisopropylamine, N,N-dimethylaniline and the like. Among them, pyridine and triethylamine are preferred. Any solvent not inhibiting the reaction may be used without any particular restriction. Thus, for example, toluene, acetone, acetonitrile, tetrahydrofuran, N,N-dimethylformamide, methylene chloride and chloroform may be mentioned. The organic base mentioned above may be used singly as such.

The base is used generally in an amount of 1.0 to 50 moles per mole of the compound (6). The reaction temperature is generally 0° C. to 60° C., preferably 0° C. to 25° C. The reaction time is generally 1 to 48 hours, desirably about 20 to 48 hours, although it may vary depending on the amounts of the sulfonic acid halide and base used.

The thus-formed sulfonate ester (7) can be recovered by neutralizing the base by addition of a mineral acid such as hydrochloric acid, followed by extraction with an organic solvent such as ethyl acetate. It can be further purified by such techniques as column chromatography and/or recrystallization.

The epoxidation step is conducted in the presence of an inorganic base. Useful as the inorganic base are, for example, sodium carbonate, potassium carbonate, sodium hydrogencarbonate, potassium hydrogencarbonate, sodium acetate and potassium acetate. Potassium carbonate is preferred, however. The inorganic base is used generally in an amount of 0.05 to 5.0 moles, preferably 0.5 to 2.0 moles, per mole of the compound (7). Usable as the solvent are methanol plus an organic solvent such as toluene, tetrahydrofuran, diethyl ether, dioxane or t-butyl methyl ether. Methanol may be used alone. A mixed solvent composed of methanol and THF (1:1 by volume) is preferred. The reaction temperature is generally 0° C. to 60° C., preferably 25 ° C. to 30° C. The reaction time is generally 1 to 24 hours, preferably 6 to 12 hours.

EXAMPLES

The following examples illustrate the present invention in further detail. They are, however, by no means limitative of the scope of the invention.

Example 1

(2S, 3S)-1-Acetoxy-3-(t-butoxycarbonylamino)-2-hydroxy-4-phenylbutane

A mixture composed of 2.0 mmol (0.599 g) of (2S, 3S)-3-(t-butoxycarbonylamino)-1-chloro-2-hydroxy-4-phenylbutane, 2.4 mmol (0.724 g) of tetrabutylammonium acetate and 10 ml of acetonitrile was stirred under reflux for 18hours. Thereafter, the solvent was distilled off under reduced pressure, 20 ml of water and 20 ml of ethyl acetate were added, and the organic layer was separated, dried over sodium sulfate, filtered and concentrated under reduced pressure to give a crude product. This was dissolved in 10 ml of methanol with heating and the solution was cooled and allowed to stand. The resulting crystalline precipitate was collected by filtration, whereupon 0.449 g (70%) of the title compound was obtained.

$^1$H-NMR (400 MHz, CDCl$_3$) δ 1. 37 (s, 9H), 2.11 (s, 3H), 2.84–2.97 (m, 2H), 3.36 (br, 1H), 3.88–3.91 (m, 2H), 4.12 (dd, 1H, J=11.7 Hz, 3.2 Hz), 4.59–4.76 (m, 1H), 7.20–7.32 (m, 5H).

$^{13}$C-NMR (100 MHz, CDCl$_3$) δ 20.92, 28.23, 36.01, 54.24 66.24, 71.87, 80.01, 126.63, 128.57, 129.39, 137.42, 156.11, 171.34.

Example 2

(2S, 3S)-1-Acetoxy-3-(t-butoxycarbonylamino)-2-hydroxy-4-phenylbutane

A mixture composed of 2.0 nmmol (0.524 g) of (2S, 3S)-3-(t-butoxycarbonylamino)-4-phenylbutane-1,2-epoxide, 2.4 mmol (0.724 g) of tetrabutylammonium acetate, 4.0 mmol (0.24 g) of acetic acid and 10 ml of acetonitrile was stirred under reflux for 18 hours. Thereafter, the solvent was distilled off under reduced pressure, 20 ml of water and 20 ml of ethyl acetate were added, and the organic layer was separated, dried over sodium sulfate, filtered and concentrated under reduced pressure to give a crude product. Purification by silica gel column chromatography gave 0.415 g (64%) of the title compound.

Example 3

(2S, 3S)-1-Acetoxy-3-(t-butoxycarbonylamino)-2-hydroxy-4-phenylbutane

A mixture composed of 2.0 mmol (0.599 g) of (2S, 3S)-3-(t-butoxycarbonylamino)-1-chloro-2-hydroxy-4-phenylbutane, 0.1 mmol (0.032g) of tetrabutylammoniumbromide, 5.0mmol (0.49 g) of potassium acetate and 10 ml of acetonitrile was stirred under reflux for 50 hours. Thereafter, the solvent was distilled off under reduced pressure, 20 ml of water and 20 ml of ethyl acetate were added, and the organic layer was separated, dried over sodium sulfate, filtered and concentrated under reduced pressure to give a crude product. Quantitative analysis was curried out by high performance liquid chromatography using ethylbenzene as an internal standard. Thus was obtained 0.289 g (45%) of the title compound.

Example 4

(2S, 3S)-1-Acetoxy-3-(t-butoxycarbonylamino)-2-methanesulfonyloxy-4-phenylbutane A mixture composed of 12.4 mmol (4.00 g) of (2S, 3S)-1-acetoxy-3-(t-butoxycarbonylamino)-2-hydroxy-4-phenylbutane, 24.8 mmol (2.48 g) of methanesulfonyl chloride and 20 ml of pyridine was allowed to stand at 4° C. for 48 hours. Thereafter, 30 ml of ethyl acetate was added, the organic layer was washed with three 30-ml portions of 10% hydrochloric acid and finally with 30 ml of water. The organic layer was separated, dried over sodium sulfate, filtered and concentrated under reduced pressure. Hexane (30 ml) was added to the residue, and the mixture was allowed to stand. The resulting white solid precipitate was collected by filtration. Thus was obtained 4.90 g (98%) of the title compound.

$^1$H-NMR (400 MHz, CDCl$_3$) δ 1.34 (s, 9H), 2.11 (s, 3H), 2.76 (m, IH), 3.00 (dd, 1H, J=4.9, 14.2 Hz), 3.11 (s, 3H), 4.15 (br, 1H), 4.21 (dd, 1H, J=7.3, 12.7 Hz), 4.35–4.38 (m, 1H), 4.66–4.68 (m, 1H), 5.01 (br, 1H), 7.20–7.33 (m, 5H).
$^{13}$C-NMR (100 MHz, CDCl$_3$) δ 20.75, 2.8.15, 35.85, 38.72, 52.04, 62.96, 80.02, 80.82, 126.85, 128.63, 129.10, 136.55, 155.221, 170.27.

Example 5

(2R, 3S)-3-(t-Butoxycarbonylamino)-4-phenylbutane 1,2-epoxide

A mixture composed of 1.0 mmol (0.401 g) of (2S, 3S)-1-acetoxy-3-(t-butoxycarbonylamino)-2-methanesulfonyloxy-4-phenylbutane, 2.2 mmol (0.304 g) of potassium carbonate, 10 ml of methanol and 10 ml of tetrahydrofuran was stirred at 25° C. for 20 hours. Thereafter, 10 ml of ethyl acetate and 10 ml of water were added for extraction of the product. The organic layer was separated, dried and the solvent was distilled off under reduced pressure to give a crude product. Purification by silica gel column chromatography gave 0.236 g (90%) of (2R, 3S)-3-(t-Butoxycarbonylamino)-4-phenylbutane 1,2-oxirane.

$^1$H-NMR (400 MHz, CDCl$_3$) δ 1.38 (5, 9H), 2.76–2.81 (m, 2H), 2.83–2.99 (m, 3H), 3.76 (br s, 1H), 4.45 (br, 1H), 7,21–7.33 (m, 5H)

$^{13}$C-NMR (100 MHz, CDCl$_3$) δ 28.26, 37.58, 46.91, 53.03, 53.20, 80.03, 126.68, 128.55, 129.46, 136.69, 155.21.

INDUSTRIAL APPLICABILITY

According to the present invention, it is possible to produce the desired (2R, 3S)-3-amino-1,2-oxirane (8) efficiently via three steps from the (2S, 3S)-3-amino-1-halo-2-hydroxy-4-phenylbutane compound (1) or (2S, 3S)-3-amino-1,2-oxirane compound (2) The above starting compounds can be readily synthesized from L-phenylalanine. Thus, in other words, the (2S, 3S)-3-amino-phenylbutane-1,2-epoxide compound (8) can be produced from L-phenylalanine.

What is claimed is:

1. A (2S, 3S)-1-acyloxy-3-amino-2-sulfonyloxy-4-phenylbutane compound represented by the general formula (7):

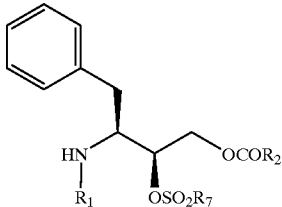

(7)

wherein R$_1$ represents an amino-protecting group and R$_2$ and R$_7$ each independently represent an alkyl, aryl or aralkyl group.

2. The compound according to claim 1, wherein R$_1$ represents t-butoxycarbonyl group, methoxycarbonyl group, ethoxycarbonyl group or benzyloxycarbonyl group.

3. The compound according to claim 1, wherein R$_2$ represents an alkyl group.

4. The compound according to claim 3, wherein R$_2$ represents methyl group.

5. The compound according to claim 1, wherein R$_7$ represents methyl group or p-methylphenyl group.

6. The compound according to claim 2, wherein R$_2$ represents an alkyl group.

7. The compound according to claim 6, wherein R$_2$ represents methyl group.

8. The compound according to claim 2, wherein R$_7$ represents methyl group or p-methylphenyl group.

9. The compound according to claim 3, wherein R$_7$ represents methyl group or p-methylphenyl group.

10. The compound according to claim 4, wherein R$_7$ represents methyl group or p-methylphenyl group.

11. The compound according to claim 6, wherein R$_7$ represents methyl group or p-methylphenyl group.

12. The compound according to claim 7, wherein R$_7$ represents methyl group or p-methylphenyl group.

* * * * *